United States Patent [19]

Elias-Geisseler

[11] 4,196,733
[45] Apr. 8, 1980

[54] DIAPER COMPRISING A PLURALITY OF SUPERIMPOSED PLIES

[76] Inventor: Marlies Elias-Geisseler, Im Vogelsang, Elm, Switzerland

[21] Appl. No.: 847,990

[22] Filed: Nov. 2, 1977

[30] Foreign Application Priority Data

Nov. 5, 1976 [CH] Switzerland .................. 14009/76

[51] Int. Cl.² .......................................... A61F 13/16
[52] U.S. Cl. .................................. 128/287; 128/284
[58] Field of Search ................... 128/284, 287, 290

[56] References Cited

U.S. PATENT DOCUMENTS

| | | | |
|---|---|---|---|
| 3,563,242 | 2/1971 | Hedstrom | 128/287 |
| 3,774,610 | 11/1973 | Eckert et al. | 128/287 |
| 3,838,693 | 10/1974 | Sherman | 128/287 |
| 3,918,433 | 11/1975 | Fuisz | 128/284 |

*Primary Examiner*—Robert W. Michell
*Assistant Examiner*—C. W. Shedd
*Attorney, Agent, or Firm*—Ladas, Parry, Von Gehr, Goldsmith & Deschamps

[57] ABSTRACT

A diaper comprising a plurality of superimposed plies of material. The diaper is foldable around a center line defining two sections of the diaper. In use the diaper is in its folded state and for washing and drying the diaper is in an unfolded state.

2 Claims, 4 Drawing Figures

DIAPER COMPRISING A PLURALITY OF SUPERIMPOSED PLIES

BACKGROUND OF THE INVENTION

1. FIELD OF THE INVENTION

The present invention relates to a diaper comprising a plurality of superimposed plies of material. Such material encompasses washable and reusable textile products manufactured of natural or man-made fibres.

2. DESCRIPTION OF THE PRIOR ART

Conventional diapers which are reusable are generally available as individual, separately folded textile products which are used together with trousers fabricated of rubber. Furthermore the prior art encompasses sponge-type diapers manufactured in specific forms and disposable diapers ("pampers") and disposable trousers.

Diapers manufactured of a textile material feature the drawback that due to a shifting of the individual diaper there are formed folds which define areas of pressure generating an inconvenience for the babies. The disposable diapers and pants can be used only once such that their costs is high.

SUMMARY OF THE INVENTION

It is an object of the invention to provide a reusable, absorbent, skin-friendly diaper comprising a plurality of superimposed plies of material, which allows free movements of its bearer as well as a practical handling and features a short drying time.

It is a further object to provide a diaper comprising a plurality of superimposed plies of material, characterized in that each of said plies consists of a separate material differing from the material of at least an adjacent ply, further in that there is provided a waterproof covering ply, whereby all said plies are connected to each other and to said waterproof covering ply, and whereby said diaper comprises two sections and is foldable around its centerline such that in use it is in a folded state whereby said sections overlap and during washing and drying thereof the diaper is in an unfolded state.

A further object is to provide a diaper which is foldable around its longitudinal centerline.

A still further object is to provide a diaper which is foldable around its lateral centerline.

Yet a further object is to provide a diaper, the outer contour of which is symmetrical to said centerline whereby corresponding oppositely located edges extend symmetrically to said centerline.

It is a further object to provide a diaper whereby every ply is of a different material.

It is a further object to provide a diaper whereby in its folded state said two overlapping sections are releasably connected to each other.

BRIEF DESCRIPTION OF THE DRAWINGS

The present invention will be more fully understood by reference to the following detailed description thereof when read in conjunction with the attached drawings, and wherein:

Referring now to FIG. 1 there is shown a diaper according to the invention and which is identified by the reference numeral 1. This diaper is a reusable diaper consisting of several plies connected to each other and which as a unit is foldable around its centerline, or center area, respectively, shown with the reference numeral 3.

Figure 1:
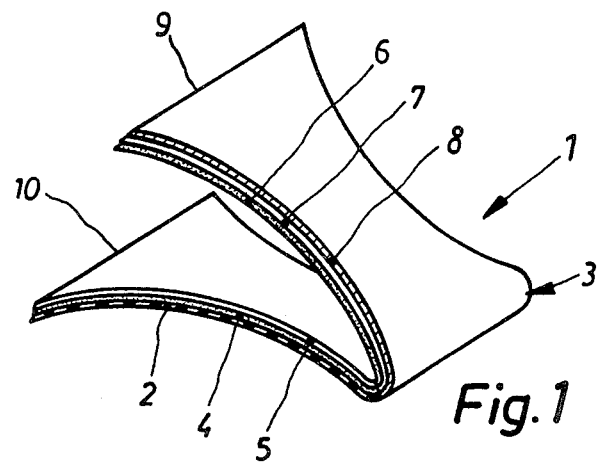
FIG. 1 is a perspective view of a diaper according to the invention, whereby the diaper is shown in section.

Beginning at the bottom of FIG. 1 the first ply 2 is a waterproof, washable, soft covering ply which will not turn brittle. The next following ply 4 is an absorbent, washable, soft textile material. The next ply 5 is a soft, nestling, skin-friendly washable textile material. Ply 6 consists of the same material as ply 4 and ply 7 consists of the same material as ply 5. Ply 8, which is the ply which contacts the human body is a water permeable, skin-friendly, elastic, soft, washable textile material.

In use, the edge areas 9 and 10 are releasably connected to each other.

Figure 2:
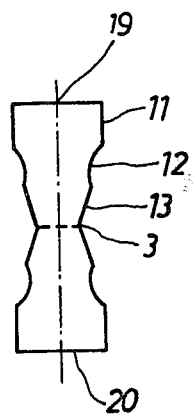
FIGS. 2 and 3 show plan views of respective embodiments of the diaper of the present invention in its unfolded state.

In FIG. 2 there is shown an embodiment of the diaper whereby its end edges 19 and 20, corresponding to the end edges 9 and 10 of FIG. 1 extend parallel to each other and the centerline 3. The diaper is formed symmetrical to its centerline 3 and its longitudinal centerline 33 intersecting centerline 3 at right angles. The end edge 19 is followed by a straight side edge 11 extending rectangularly to the end edge 11, further by a cut out portion 12 and finally by an obliquely extending straight side edge 13, ending at the centerline 3.

Figure 3:
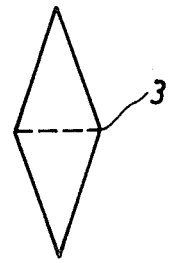

Finally, the embodiment of FIG. 3 has the form of two isosceles triangles having a common base line.

While there are shown and described present preferred embodiments of the invention, it is to be distinctly understood that the invention is not limited thereto, but may be otherwise variously embodied and practiced within the scope of the following claims.

ACCORDINGLY,

What is claimed is:

1. A reusable diaper comprising a sheet of material in the form of first and second sections which meet at a fold line, the sheet being foldable along the fold line to bring the two sections into a use condition in which the two sections are superposed and are substantially coextensive and the folded sheet can be positioned on a wearer as a diaper, and the sheet being unfoldable from the use condition to a spread out non-use condition, and wherein each of said sections is made up of at least two substantially coextensive plies and the first section of said sheet has as one of it outermost plies a layer of fluid impermeable material and as the other of its outermost plies an absorbent textile layer, while said second section has as one of its outermost plies a fluid permeable and skin-friendly layer and as the other of its outermost plies an absorbent textile layer, said adsorbent textile layer of said first section forming substantially an extension of said absorbent textile layer of said second section, so that upon folding the sheet along the fold line the absorbent textile layer of said first section can be brought into confronting relationship with said absorbent textile layer of said second section, and the folded sheet can be positioned on a wearer as a diaper with the fluid permeable and skin-friendly layer of the second section innermost, contacting the skin of the wearer, and the fluid impermeable layer of the first section outermost.

2. A diaper as claimed in claim 1, wherein each of said first and second sections is substantially rectangular in form with the two longer edges of each rectangle being concaved and the fold line extending along one of the shorter edges of each rectangle.

* * * * *